T

(12) United States Patent
Comp

(10) Patent No.: US 7,291,333 B1
(45) Date of Patent: Nov. 6, 2007

(54) BLOCKADE OF PROTEIN C ACTIVATION REDUCES MICROVASCULAR SURGICAL BLOOD LOSS

(75) Inventor: Philip C. Comp, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 08/323,060

(22) Filed: Oct. 14, 1994

Related U.S. Application Data

(63) Continuation of application No. 07/919,219, filed on Jul. 24, 1992, now abandoned.

(51) Int. Cl.
*A61K 39/395* (2006.01)
*C07K 16/44* (2006.01)
*C07K 16/18* (2006.01)

(52) U.S. Cl. .............. 424/145.1; 424/139.1; 424/152.1; 424/158.1; 424/172.1; 514/2; 514/834; 530/388.25; 530/389.3; 435/337

(58) Field of Classification Search .............. 424/85.8, 424/139.1, 145.1, 152.1, 158.1, 172.1, 94.1, 424/94.64; 514/834, 2; 530/381, 388.25, 530/389.3, 380, 388.85; 435/69.6, 70.21, 435/172.2, 240.25, 337; 935/89, 104, 107
See application file for complete search history.

(56) References Cited

U.S. PATENT DOCUMENTS

| | | | |
|---|---|---|---|
| 5,084,273 A | 1/1992 | Hirahara | 424/94.6 |
| 5,093,117 A | 3/1992 | Lawrence et al. | 424/85.8 |
| 5,130,244 A * | 7/1992 | Nishimaki et al. | 435/188 |
| 5,147,638 A * | 9/1992 | Esmon et al. | 424/85.8 |
| 5,202,253 A * | 4/1993 | Esmon et al. | 435/240.27 |

FOREIGN PATENT DOCUMENTS

WO    WO 94/22470    10/1994

OTHER PUBLICATIONS

Suzuki et al. Thrombosis Research 53; 271-277, 1989.*
Waldmann, Science, vol. 252, 1657-62, 1991.*
Harris et al., TIBTECH, vol. 11, p. 42-44, 1993.*
Broze, Sem. Hematol. , vol. 29, 159-169, 1992.*
Taylor et al., Trauma, 30, 5197-203, 1990.*
Taylor et al., J. Clin. Inv., 79, 918-925, 1987.*
Taylor et al., Blood, 78, 357-363, 1991.*
Rhein, Biotechnology Newswatch, Oct. 4, 1993, pp. 1 and 3.*
Fusker et al., "Spontaneous Arterial Lesions in Normal Pigs With Von Willebrand's Disease" pp. 315-317, From: Artherosclerosis Metabolic, Morphologic and Clinical Aspects, Ed. G. W. Manning, Plenum Press, 1977.*
Fusker et al., "Interactions of Platelets With the Endothelium in Normal and Von Willebrand Pigs", pp. 187-196, From Thrombosis Animal and Clinical Models, Ed. H. J. Day et al., Plenum Press, 1977.*
Bowie et al., J. Clin. Inv., 78: 26-30, 1986.*
Cheesebro et al., Circulation, 86, No. 6, Supplement III, 100-110, 1992.*
Fass et al., Thrombosis Res., 8: 319-327, 1976.*
Montagwa et al., J. Inv. Derm., 43:11-22, 1964.*
Griggs et al., Am. J. Path., 102:137-145, 1981.*
Furie et al. , Cell, 53: 505-518, 1988.*
Bauer, K.A. and R. D. Rosenbrg, "Congenital antithrombin III deficiency: Insights into the pathogenesis of the hypercoagulable state and its management using markers of hemostatic system activation," *Am.J.Med.* 87:39S-43S (1989).
Bauer, K.A. and R.D. Rosenberg, "Role of antithrombin III as a regulator of in vivo coagulation," *Semin.Hematol.* 28:10-18 (1991).
Broze, G.J., Jr., et al., "The lipoprotein-associated coagulation inhibitor," *Prog.Hemost.Thromb.* 10:243-268 (1991).
Broze, G.J., Jr., et al., "Regulation of coagulation by a multivalent Kunitz-type inhibitor," *Biochemistry.* 29:7539-7546 (1990).
Chesebro, James H., et al., "Antithrombotic Therapy and Proression of Coronary Artery Disease," *Circulation Supplement III*, 86(6):III-100-!!!-110 (1992).
Clouse, L.H. and Comp, P.C., "The regulation of hemostatis: The protein C system," *N, Engl. J. Med.* 314(20):1298 (1986).
Comp, P.C. and Esmon, C.T., "Generation of fibrinolytic activity by infusion of activated protein C into dogs," *J. Clin. Invest.* 68:1221 (1981).
Comp, P.C., et al. , "Familial protein S deficiency is associated with recurrent thrombosis," *J. Clin, Invest.* 74:2082-2088 (1984).
Comp, P.C., et al., "Activation of protein C in vivo," *J.Clin.Invest.* 70: 127-134 (1987).
Comp. P.C., "Hereditary disorders predisposing to throbosis," In B.S. Coller (Ed.), *Progress in Hemostasis and Thrombosis*. (New York: Grune and Stratton, 1986). vol. 8, pp. 71-102.
Conway, E.M. and R.D. Rosenberg, "Tumor necrosis factor suppresses transcription of the thrombomodulin gene in endothelial cells," *Mol.Cell.Biol.* 8:5588-5592 (1988).
Cooper, D.K.C., et al., "The Pig as Potential Organ Donor for Man," Chapter 30, 481-500.
Dahlback, B., "Interaction between vitamin K-dependent protein S and the complement protein, C4b-binding protein. A link between coagulation and the complement system," *Semin.Thromb.Hemost.* 10:139-148 (1984).
Dahlback, B., "Inhibition of protein Ca cofactor function of human and bovine protein S by C4b-binding protein," *J.Biol.Chem.* 261:12022-12027 (1986).
Dahlback, B., "Interaction between complement component C4b-binding protein and the vitamin K-dependent protein S. A link between blood coagulation and the complement system," *Scand.J. Clin.Lab.Invest.* [Suppl] 177:33-41 (1985).
de Fouw, N.J., et al., "The cofactor role of protein S in the acceleration of whole blood clot lysis by activated protein C in vitro," Blood 67:1189-1192 (1986).
Esmon, C.T,, et al., "Interaction of thrombin with thrombomodulin," *Ann. N.Y. Acad. Sci.* 485: 215 (1986).
Esmon, C.T., "The roles of protein C and thrombomodulin in the regulation of blood coagulation," *J. Biol. Chem.* 264(9): 4743 (1989).

(Continued)

Primary Examiner—Ronald B. Schwadron
(74) Attorney, Agent, or Firm—Fulbright & Jaworski, LLP

(57) ABSTRACT

A method of inhibiting microvascular bleeding is provided. Antibody to protein C administered to a patient in a pharmaceutically acceptable carrier prevents anticoagulation by greater than 90% of activated protein C in human plasma.

5 Claims, 3 Drawing Sheets

OTHER PUBLICATIONS

Esmon, N.L., "Thrombomodulin," Semin.Thromb.Hemost. 13:454-463 (1987).

Flaherty, M.J., et al. "Iatrogenic immunization with bovine thrombin: A mechanism for prolonged thrombin times after surgery," *Ann. Int. Med.* 111: 631 (1989).

Flaherty, M.J. and Wener, M.H., "Antibodies to thrombin in post-surgical patients," *Blood* 73(5):1386 (1989).

Fulcher, C.A. et al., "Proteolytic inactivation of human factor VIII procoagulant protein by activated human protein C and its analogy with V," *Blood* 63:486-49 (1984).

Hillarp, A. and B. Dahlback, "The protein S-binding site localized to the central core of C4b-binding protein," *J. Biol. Chem.* 262:11300-11307 (1987).

Kirkman, Robert L., "Of swine and men: organ physiology in different species," *Xenograft* 25 Mark A. Hardy (Ed.), 1989 Elsevier Science Publishers (Biomedical Division).

Kisiel, W., et al., "Anti-coagulant properties of bovine plasma protein C following activation by thrombin," *Biochemistry* 16: 5824 (1977).

Kisiel, W., "Human plasma protein C: Isolation, characterization and mechanism of activation by alpha-thrombin," *J. Clin. Invest.* 64:761 (1979).

Lentz, S.R., et al., "Regulation of thrombomodulin by tumor necrosis factor-alpha: comparison of transcriptional and post-transcriptional mechanism," *Blood* 77:542-550 (1991).

Marlar, R.A., et al., "Human protein C: inactivation of factors V and VIII in the activated molecule," *Ann.NY.Acad.Sci.* 370:303-10 (1981).

Melissari and Kakkar, "Congenital severe protein C deficiency in adults," *Br. J. Haematol.* 72(2):222-228 (1989).

Menache, D., "Antithrombin III: introduction," *Semin.Hematol.* 28:1-2 (1991).

Miletich, J.P., "Laboratory diagnosis of protein C deficiency," *Semin. Thromb. Hemost.* 16(2):169 (1990).

Miletich, J., et al., "Absence of thrombosis in subjects with heterozygous protein C deficiency," *N. Engl. J. Med.* 317(16):991 (1987).

Moore, K., et al., "Endotoxin enhances tissue factor and suppresses thrombomodulin expression of human vascular endothelium in vitro," *J.Clin.Invest.* 79:124-130 (1987).

Moore, K.L., et al., "Tumor necrosis factor leads to the internalization and degradation of thrombomodulin from the surface of bovine aortic endothelial cells in culture Indianapolis," *Blood* 73:159-165 (1989).

Muller, James E., "Coronary Artery Thrombosis: Historical Aspects," *J. Am. Coll. Cardiol.* 1(3):893-896 (1983).

Nawroth, P.P., et al., "Interleukin 1 induces endothelial cell procoagulant while suppressing cell-surface anticoagulant activity," *Proc.Natl.Acad.Sci.USA* 83:3460-344 (1986).

Nawroth, P.P. and D.M. Stern, "Modulation of endothelial cell hemostatic properties by tumor necrosis factor," *J.Exp.med.* 163:740-745 (1986).

Owen, W.G. and Esmon, C.T., "Functional properties of an endothelial cell cofactor for thrombin-catalyzed activation of protein C," *J. Biol. Chem.* 256:5532 (1981).

Prelssner, K.T., "Biological relevance of the protein C system and laboratories diagnosis of protein C and protein S deficiencies," *Clin. Sci.* 78: 351, 1990.

Rapaport, S.I., "Inhibition of factor VIIa/tissue factor-induced blood coagulation: with particular emphasis upon a factor Xa-dependent inhibitory mechanism 92013," *Blood* 73:359-365 (1989).

Rapaport. S.I., "The extrinsic pathway inhibitor: a regulator of tissue factor-dependent blood coagulation," *Thromb.Haemost.* 66 (1):6-15 (1991).

Snow, T.R., et al., "Protein C activation following coronary artery occlusion in the in situ porcine heart," *Circulation* 84:(1): 293 (1991).

Stearns, D.J., et al., "The interaction of a $Ca^{2+}$-dependent monoclonal antibody with the protein C activation peptide region. Evidence for obligatory $Ca^{2+}$ binding to both antigen and antibody," *J. Biol. Chem.* 263: 826-832 (1988).

Stricker, R.B., et al., "Development of antithrombin antibodies following surgery in patients with prosthetic cardiac valves," *Blood* 72(4):1375 (1988).

Taylor, F.B., et al., "Protein C prevents the coagulopathic and lethal effects of *Escherichia coli* infusion in the baboon," *J. Clin. Invest.* 79: 918 (1987).

Tripodi, A., et al., "Asymptomatic homozygous protein C deficiency," *Acta. Haemato*l. 83: 152 (1990).

Tuddenham, E.G., et al., "Homozygous protein C deficiency with delayed onset of symptoms at 7 to 10 months," *Thromb. Res.* 53: 475 (1989).

Walker, F.J., "Protein C deficiency in liver disease," *Ann. Clin. Lab. Sci.* 20(2):106 (1990).

Walker, F.J., Scandella, D. and Fay P.J., "Identification of the binding site for activated protein C on the light chain of factors V and VIII," *J. Biol. Chem.* 265(3):1484-89 (1990).

Walker, F.J., "Regulation of activated protein C by protein S. The role of phospholipid in factor Va inactivation," *J.Biol.Chem.* 256:11128-11131 (1981).

Walker, F.J., "Protein S and the regulation of activated protein C," *Semin.Thromb.Hemost.* 10:131-138 (1984).

Walker, F.J., "Interactions of protein S with membranes," *Semin. Thromb.Hemost.* 14:216-221 (1988).

Walker, F.J., et al., "Inactivation of factor VIII by activated protein C and protein S," *Arch.Biochem.Biophys.* 252:322-328 (1987).

Walker, F.J., "Regulation of activated protein C by a new protein. A possible function for bovine protein S," *J.Biol.Chem.* 255:5521-5524 (1980).

\* cited by examiner ptu

SEQUENCE LISTING

```
<160> NUMBER OF SEQ ID NOS: 1

<210> SEQ ID NO 1
<211> LENGTH: 12
<212> TYPE: PRT
<213> ORGANISM: Homo sapiens

<400> SEQUENCE: 1

Glu Asp Gln Val Asp Pro Arg Leu Ile Asp Gly Lys
 1               5                   10
```

BLOCKADE OF PROTEIN C ACTIVATION REDUCES MICROVASCULAR SURGICAL BLOOD LOSS This is a continuation of application Ser. No. 07/919,219 filed on Jul. 24, 1992 (now abandoned).

BACKGROUND OF THE INVENTION

Microvascular (capillary) bleeding is a significant source of blood loss in many conditions including bleeding liver surfaces, skin graft donor sites, inflamed visceral surfaces, and burns. Because of the diffuse nature of this type of bleeding, vessel ligation or electrocautery is not a feasible method of hemostasis. Currently, the dominant method of treatment of this type of bleeding is topical thrombin and direct pressure applied to the bleeding surface.

However, during traumatic cerebral, retroperitoneal, and pelvic hemorrhage, surgical exposure of microvascular bleeding sites can actually worsen the hemorrhage, making topical agents undesirable. Additionally, bovine antithrombin antibodies have been reported in many postoperative patients receiving topical thrombin intraoperatively causing prolongation of prothrombin time, activated partial thromboplastin time, and thrombin time up to 12-fold, as reported by Flaherty, M. J. and Wener, M. H. Antibodies to thrombin in postsurgical patients. *Blood* 73(5): 1386 (1989); Stricker, R. B., et al., Development of antithrombin antibodies following surgery in patients with prosthetic cardiac valves. *Blood* 72(4): 1375 (1988); Flaherty, M. J., et al. Iatrogenic immunization with bovine thrombin: A mechanism for prolonged thrombin times after surgery. *Ann. Int. Med.* 111: 631 (1989).

It is not possible to administer thrombin systemically since this could clearly result in massive systemic clotting.

It is therefore an object of the present invention to provide an alternative therapy for microvascular bleeding.

It is a further object of the present invention to provide a therapy which can be administered systemically or topically.

SUMMARY OF THE INVENTION

It has been discovered that by temporarily blocking one or more natural anticoagulants, such as the activation of intrinsic protein C, subsequent surgical or traumatic blood loss from a microvascular surgical or traumatic wound can be substantially reduced. Other natural anticoagulants include thrombomodulin, heparin cofactor II, antithrombin III, and tissue factor inhibitor pathway. The formation of activated protein C can be blocked systemically by intravenous administration of a monoclonal antibody ($HPC_4$) which binds irreversibly to circulating protein C, effectively covering its activation site and therefore blocking any subsequent activation of the affected protein C molecule. The antibody is specific for the inactive form of protein C and does not bind to previously activated protein C or any other clotting cofactors.

The effects of protein C blockade were compared to the standard therapy, topical thrombin, and to the experimental topical agent, tissue thromboplastin. Domestic pigs were blindly pretreated with intravenous $HPC_4$ or saline then underwent partial-thickness skin graft harvesting to create a reproducible microvascular wound. Blood loss was measured from each wound and the hemostatic effect of protein C blockade was compared to intravenous saline alone as well as to topical thrombin or thromboplastin. It was found that blocking the activation of protein C significantly (P=0.005) reduces surgical blood loss in this model by 27% compared to saline control animals. Intravenous $HPC_4$ performed equally as well as topical thrombin or tissue thromboplastin. In addition, topical thrombin acted synergistically with $HPC_4$ to reduce blood loss an additional 44% (P=0.01) as compared to intravenous $HPC_4$ or topical thromboplastin alone. Autopsies performed one week after $HPC_4$ treatment showed no evidence of systemic thrombosis resulting from the protein C blockage. This study reveals that blocking the formation of the natural anticoagulant, activated protein C prior to surgery provides a systemic means of reducing capillary bleeding from vascular beds.

DETAILED DESCRIPTION OF THE INVENTION

Figure 1:
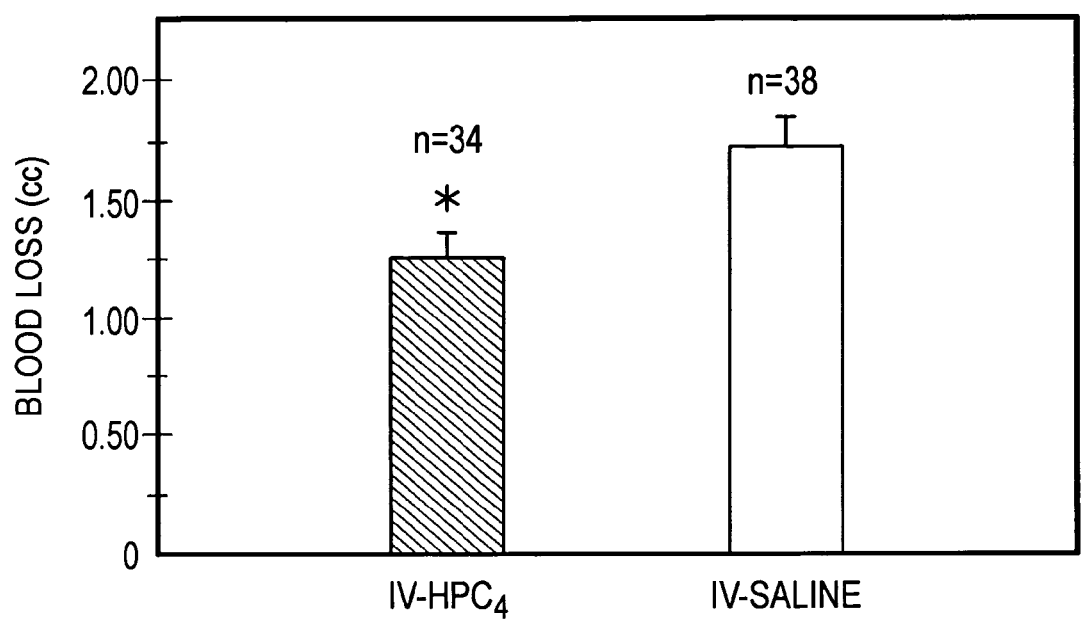
FIG. 1 is a graph of blood loss (cc) in i.v. HPC4 and i.v. saline treated animals showing hemostasis with systemic $HPC_4$ blockade compared to controls. Blood loss from each 7×8 cm surgical site is collected over 10 min and represented as mean milliliters±SEM. The solid black bar depicts animals pretreated with systemic $HPC_4$ (n=34 sites) and is compared to the white bar depicting animals receiving systemic saline (n=36 sites). Statistical analysis: two-tailed Student's t test.

It has been discovered that natural anticoagulants can be blocked systemically or topically and inhibit microvascular clotting without initiating widespread coagulation. Based on this discovery, it is possible to selectively inhibit microvascular coagulation by systemic administration of an inhibitor of a natural anticoagulant, such as protein C, alone or in combination with topical administration of a coagulant such as thrombin or tissue thromboplastin.

Protein C is a 62,000 Da plasma glycoprotein precursor of a serine protease-labeled activated protein C, as reported by Miletich, J. P. Laboratory diagnosis of protein C deficiency. *Semin. Thromb. Hemost.* 16(2): 169 (1990). Proteolytic cleavage to form activated protein C from its inactive precursor occurs at a specific arginine-leucine bond located on the heavy chain 12 amino acids from the amino terminal, as reported by Kisiel, W. Human plasma protein C: Isolation, characterization and mechanism of activation by alpha-thrombin. *J. Clin. Invest.* 64: 761 (1979). Although this cleavage is initiated by thrombin, as described by Clouse, L. H. and Comp, P. C. The regulation of hemostasis: The protein C system. *N. Engl. J. Med.* 314(20): 1298 (1986), the endothelium-bound cofactor thrombomodulin is able to catalyze the thrombin activation of protein C increasing the reaction time 20,000-fold. Calcium is able to further enhance the activation of protein C by thrombin-thrombomodulin an additional 50-fold, as reported by Esmon, C. T. The roles of protein C and thrombomodulin in the regulation of blood coagulation. *J. Biol. Chem.* 264(9): 4743 (1989). Once activated, protein C acts as an endogenous anticoagulant increasing clotting times up to 3-fold in vitro, as reported by Owen, W. G. and Esmon, C. T. Functional properties of an endothelial cell cofactor for thrombin-catalyzed activation of protein C. *J. Biol. Chem.* 256: 5532 (1981). Its anticoagulant properties have been related to the inactivation of factor VIIIa, the proteolytic degradation of factor Va, and the neutralization of an inactivator of plasminogen activator, as described by Walker, F. J., Scandella, D. and Fay P. J. Identification of the binding site for activated protein C on the light chain of factors V and VIII. *J. Biol. Chem.* 265(3): 1484-89 (1990); Preissner, K. T. Biological relevance of the protein C system and laboratories diagnosis of protein C and protein S deficiencies. *Clin. Sci.* 78: 351 (1990); Comp, P. C. and Esmon, C. T. Generation of fibrinolytic activity by infusion of activated protein C into dogs. *J. Clin. Invest.* 68: 1221 (1981); resulting in prolongation of the prothrombin and activated partial thromboplastin time but not the thrombin time, as reported by Comp, P. C. and Esmon, C. T. Generation of fibrinolytic activity by infusion of activated protein C into dogs. *J. Clin. Invest.* 68: 1221 (1981); Kisiel, W., et al., Anti-coagulant properties of bovine plasma protein C following activation by thrombin. *Biochemistry* 16: 5824 (1977). Activated protein C is formed at the site of the endothelial injury in response to blood clotting and helps limit the size of blood clots.

Blocking of protein C activation was demonstrated to be effective in stopping microvascular bleeding using skin graft harvesting. Skin graft harvesting was chosen because of the reproducibility of the wound it afforded and the reliable access to blood loss collection. In addition to testing the antibody's effects against controls receiving intravenous saline, the effect of the antibody was also compared to the topical thrombogenic agents, thrombin and tissue thromboplastin, both as a way to judge the degree of hemostasis against a relative standard and to evaluate any synergistic effect between the intravenous antibody and the topical treatments.

Natural Anticoagulants and Agents that Inhibit them.

In general, any compound that specifically, and rapidly, blocks one or more of the natural anticoagulant proteins can be used. Most preferably, a compound preventing activation of protein C or the enzymatic activity of activated protein C is used to prevent microvascular bleeding. The compound must be non-toxic and specific, so that adverse side effects do not occur, and not lead to uncontrolled clotting. As used herein, an "anti-protein C" compound refers to any agent which specifically inhibits either the activation of protein C, the enzymatic activity of activated protein C, or other component of the protein C complex such as protein S or C4B binding protein.

The Natural Anticoagulant Proteins.

Protein C.

Biochemistry: Protein C is a vitamin K-dependent plasma protein whose structure closely resembles the vitamin K-dependent clotting proteins such as prothrombin. Although protein C was discovered in 1960, demonstration that the protein was involved in the regulation of coagulation took considerably longer. The ability of thrombin to convert protein C to an active anticoagulant, called activated protein C, was recognized early. However, the activation of protein C by this mechanism was very slow, too slow in fact to be of much significance in vivo. The body simply could not generate enough thrombin to activate an appreciable amount of activated protein C. The major breakthrough came when Esmon and Owen discovered that thrombin forms a complex with thrombomodulin, a protein on the surface of endothelial cells, and that thrombomodulin-bound thrombin rapidly converts protein C to activated protein C, reported by Esmon, N. L., Thrombomodulin. Semin. Thromb. Hemost. 13:454-463 (1987). In vivo the generation of thrombin by intravascular clotting results in the formation of thrombin-thrombomodulin complex in the capillary beds of the body. This complex then converts protein C into activated protein C which in turn limits further blood clotting. The role of thrombin in the activation of protein C can be demonstrated in animal models. The infusion of low levels of thrombin results in the generation of significant quantities of activated protein C and anticoagulation of the animal as determined by clotting time prolongation, as described by Comp, P. C., et al., Activation of protein C in vivo. *J. Clin. Invest.* 70: 127-134 (1987).

Activated protein C functions as an anticoagulant by enzymatically degrading two activated coagulation factors, factor Va and factor VIIIa, as described by Esmon, N. L., Thrombomodulin. *Semin. Thromb. Hemost.* 13:454-463 (1987); Fulcher, C. A., et al., Proteolytic inactivation of human factor VIII procoagulant protein by activated human protein C and its analogy with V. *Blood* 63:486-49 (1984); Marlar, R. A., et al., Human protein C: inactivation of factors V and VIII in the activated molecule. *Ann. NY. Acad. Sci.* 370:303-10 (1981); Walker, F. J., et al., Inactivation of factor VIII by activated protein C and protein S. *Arch. Biochem. Biophys.* 252:322-328 (1987). These two proteins catalyze the clotting cascade by speeding the conversion of prothrombin to thrombin and factor X to its active form (factor Xa). The enzymatic degradation of these cofactor proteins by activated protein C rapidly slows the clotting process and results in anticoagulation.

Protein S and C4B Binding Protein.

By itself, activated protein C is not a good anticoagulant. Activated protein C requires another vitamin K-dependent plasma protein, protein S, in order to function as an anticoagulant, as reported by Walker, F. J., Interactions of protein S with membranes. *Semin. Thromb. Hemost.* 14:216-221 (1988); Walker, F. J., 1984. Protein S and the regulation of activated protein C. *Semin. Thromb. Hemost.* 10:131-138 (1984); Walker, F. J. Regulation of activated protein C by protein S. The role of phospholipid in factor Va inactivation. *J. Biol. Chem.* 256:11128-11131 (1981); Walker, F. J. Regulation of activated protein C by a new protein. A possible function for bovine protein S. *J. Biol. Chem.* 255:5521-5524 (1980); and de Fouw, N. J., et al. The cofactor role of protein S in the acceleration of whole blood clot lysis by activated protein C in vitro. *Blood* 67:1189-1192 (1986). Although protein S is very similar in structure to protein C, prothrombin, and the other vitamin K-dependent plasma protein, it differs in two critical points.

First, protein S lacks the amino acid structure to become an active enzyme. It functions by increasing the anticoagulant effects of activated protein C. Secondly, protein S exists in two forms in plasma—as free protein S, the cofactor for activated protein C, and as a complexed form, as reported by Hillarp, A. and B. Dahlback, The protein S-binding site localized to the central core of C4b-binding protein. *J. Biol. Chem.* 262:11300-11307 (1987); Dahlback, B. Interaction between complement component C4b-binding protein and the vitamin K-dependent protein S. A link between blood coagulation and the complement system. *Scand. J. Clin. Lab. Invest. [Suppl]* 177:33-41 (1985); Dahlback, B. Interaction between vitamin K-dependent protein S and the complement protein, C4b-binding protein. A link between coagulation and the complement system. *Semin. Thromb. Hemost.* 10:139-148 (1984). The complexed protein S is bound to C4b binding protein, an inhibitor of the complement system, and does not serve as a cofactor for activated protein C Dahlback, B. Inhibition of protein Ca cofactor function of human and bovine protein S by C4b-binding protein. *J. Biol. Chem.* 261:12022-12027 (1986); Comp, P. C., et al. Familial protein S deficiency is associated with recurrent thrombosis. *J. Clin. Invest.* 74:2082-2088 (1984). Normally, 40% of the total protein S in plasma is free and 60% is complexed to C4b binding protein. C4b binding protein is an acute phase protein and increases in response to an inflammatory challenge. Protein S is capable of shifting between free and bound forms. This raises the possibility that acute elevations of C4b binding protein can result in a shift of protein S to the inactive, bound form with a consequent decrease in free protein S. This loss of free protein S results in a decrease in protein S activity in the plasma.

Thrombomodulin.

Measurement of the plasma levels of protein C and protein S tells relatively little about how the anticoagulant pathway is functioning. The protein C system depends on the availability of thrombomodulin on the endothelial surface. When blood clotting occurs in the body, thrombin is generated. This thrombin is carried into the capillary bed and here it binds to thrombomodulin. This complex formation completely changes the function of thrombin. Before thrombin binds to thrombomodulin, thrombin can cause clot formation by converting fibrinogen to fibrin, by converting factors V and VIII to their active forms and by activating platelets. After thrombin binds to thrombomodulin, thrombin has none of these procoagulant activities. The complexed thrombin will only convert protein C to activated protein C, thus serving to trigger the protein C anticoagulant pathway.

The formation of activated protein C depends on the availability of thrombomodulin on the endothelial cell surface. There is evidence in cell culture that the level of thrombomodulin is not constant. Inflammatory mediators such as tumor necrosis factor (Nawroth, P. P. and D. M. Stern Modulation of endothelial cell hemostatic properties by tumor necrosis factor. *J. Exp. med.* 163:740-745 (1986)); interleukin-1 (Nawroth, P. P., et al. Interleukin 1 induces endothelial cell procoagulant while suppressing cell-surface anticoagulant activity. *Proc. Natl. Acad. Sci. USA* 83:3460-344 (1986)) and endotoxin (Moore, K., et al. Endotoxin enhances tissue factor and suppresses thrombomodulin expression of human vascular endothelium in vitro. *J. Clin. Invest.* 79:124-130 (1987)) reduce the available thrombomodulin by processes involving inhibition of transcription (Conway, E. M. and R. D. Rosenberg. Tumor necrosis factor suppresses transcription of the thrombomodulin gene in endothelial cells. *Mol. Cell. Biol.* 8:5588-5592 (1988), Lentz, S. R., et al. Regulation of thrombomodulin by tumor necrosis factor-alpha: comparison of transcriptional and post-transcriptional mechanism. *Blood* 77:542-550 (1991)) and increased internalization and degradation of thrombomodulin (Moore, K. L., et al. Tumor necrosis factor leads to the internalization and degradation of thrombomodulin from the surface of bovine aortic endothelial cells in culture Indianapolis. *Blood* 73:159-165 (1989)). Inflammation may have similar effects in vivo and inflammatory challenges such as sepsis, tumors and the trauma of surgery may down-regulate the protein C system by decreasing thrombomodulin availability.

Since all of inflammation is aimed at reducing bleeding, i.e., decreasing free protein S, increasing C4B binding protein, decreasing thrombomodulin, increasing tissue factor, and decreasing fibrinolysis. This means that one could also inhibit thrombomodulin and stop microvascular bleeding the same as with anti-protein C.

Antithrombin III.

Antithrombin III is an inhibitor protein found in plasma which functions by blocking the activity of activated clotting factors such as factor Xa and thrombin. The rate at which antithrombin III inhibits clotting increases greatly in the presence of heparin which speeds the interaction of antithrombin III with the active clotting factors (Bauer, K. A. and R. D. Rosenberg. Role of antithrombin III as a regulator of in vivo coagulation. *Semin. Hematol.* 28:10-18 (1991); Menache, D. Antithrombin III: introduction. *Semin. Hematol.* 28:1-2 (1991); Bauer, K. A. and R. D. Rosenberg. Congenital antithrombin III deficiency: insights into the pathogenesis of the hypercoagulable state and its management using markers of hemostatic system activation. *Am. J. Med.* 87:39 S-43S (1989)). This enhancement of the anticoagulant activity of antithrombin III is the basis of the effectiveness of heparin therapy. The interactions of antithrombin III and heparin are complex and reflect the diversity of charge and molecular weight found in heparin molecules.

Tissue Factor Pathway Inhibitor.

Tissue factor pathway inhibitor (formerly called extrinsic pathway inhibitor or lipoprotein-associated coagulation inhibitor) blocks blood coagulation triggered by tissue factor (Rapaport, S. I. Inhibition of factor VIIa/tissue factor-induced blood coagulation: with particular emphasis upon a factor Xa-dependent inhibitory mechanism 92013. *Blood* 73:359-365 (1989); Rapaport, S. I. The extrinsic pathway inhibitor: a regulator of tissue factor-dependent blood coagulation. *Thromb. Haemost.* 66 (1):6-15 (1991); Broze, G. J., Jr., et al. The lipoprotein-associated coagulation inhibitor. *Prog. Hemost. Thromb.* 10:243-268 (1991); Broze, G. J., Jr., et al. Regulation of coagulation by a multivalent Kunitz-type inhibitor. *Biochemistry.* 29:7539-7546 (1990)). Tissue factor pathway inhibitor functions by first binding to factor Xa. This binding changes the conformation of the inhibitor. The factor Xa-bound tissue factor pathway inhibitor is then capable of inhibiting the factor VIIa which is associated with tissue factor.

Heparin Cofactor II.

Heparin cofactor II is a plasma inhibitor with heparin cofactor activity. Unlike antithrombin III which inhibits a number of activated clotting factors, heparin cofactor II only inhibits thrombin. Heparin cofactor II is not tightly bound by heparin and therefore requires relatively high concentrations of heparin to stimulate inhibitory activity. Heparin cofactor II probably relies on endogenous heparin endothelium to work.

Tissue Thromboplastin (or Tissue Factor)

Tissue thromboplastin has also been used to promote clotting of surface bleeding. However, this cannot be administered systemically.

Inhibitors of Natural Anticoagulants.

In the preferred embodiment, an anti-protein C monoclonal antibody that is specific in preventing activation of protein C is used either topically or systemically in an effective dosage to prevent microvascular bleeding. Such a murine monoclonal antibody is the subject of U.S. Pat. No. 5,202,253. The hybridoma cell line which secretes the monoclonal antibody of the present invention is designated as HPC-4, and was deposited with the American Type Culture Collection, Manassas, Va., on Nov. 2, 1998, and has public upon the grant of a patent. This $Ca^{2+}$ dependent monoclonal antibody specifically binds to a specific twelve peptide sequence (E D Q V D P R L I D G K) SEQ ID NO. 1 in the activation region of the Protein C by thrombin-thrombomodulin. The antibody can be isolated from cell culture or ascites fluid in large quantities by affinity chromatography using the peptide sequence described above bound to an immobilized substrate.

Alternatively, antibodies against activated protein C that block the active site can be utilized.

Other compounds that may be effective include compounds which inhibit Protein S, thereby inhibiting activated protein C. Other agents include those which inhibit thrombomodulin, antithrombin III, heparin cofactor II, and tissue factor inhibitor pathway. Examples of such compounds include antibodies against Protein S, thrombomodulin, antithrombin III, heparin cofactor II, and tissue factor inhibitor(s), as well as specific chemical inhibitors. Specific chemical inhibitors of activated protein can also be used.

In Combination with Other Thrombotic Agents.

As shown below in the example, administration of anti-protein C in combination with another thrombotic administered topically, such as thrombin or tissue thromboplastin, provides better results in some cases than administration of anti-protein C alone. This is somewhat surprising since the purpose of the inhibitor is to prevent or stop activation of protein C or other natural anticoagulants and these agents are known to activate or act as cofactors with the natural anticoagulants. Moreover, one would be concerned that inhibition of the anticoagulant would lead to widespread clotting, which does not occur.

This may reflect the relatively short duration of blockade of the protein C system. In patients with lifelong deficiency of protein C, protein S or AT III, only 50% of the patients have developed their first episode of thrombosis by age 27 to 30 years. Large kindreds of protein C deficient individuals have been identified with no increased incidence of thrombosis. Adults with severe (less than 5% normal levels) protein C deficiency have been reported who do not develop thrombosis until they are in their twenties, as reported by Melissari and Kakkar, *Br. J. Haematol.* 72(2):222-228 (1989).

Thrombin, from natural or recombinant sources, are commercially available for clinical use from Parke-Davis. Tissue factor can be obtained by published methodology, either by isolation from natural sources or by recombinant technology.

Disorders that can be Treated with Anti-Protein C Agents.

In the preferred embodiment, the anti-protein C agents are used to stop microvascular bleeding. As defined herein, microvascular means the venules, capillaries, and arterioles. This can be at the surface of a burn wound, where blood and lymph oozes from the capillaries in the burned tissue, or at the site of a skin graft.

In the setting of very brisk microvascular bleeding such as liver and splenic trauma, topical agents are washed away from the tissue surface with the flow of blood, reducing their effectiveness. Systemic administration of the anti-protein C agents provides a therapy to control such bleeding. Systemic administration is also beneficial for treatment of cerebral contusion which results in bleeding of brain capillaries, and in orthopedic surgical procedures involving bone cutting.

Dosages and Modes of Administration

The preferred method of administration is to systemically administer the anticoagulant inhibitor in conjunction with topical coagulant. The anticoagulant inhibitor can also be administered alone systemically, or less preferably, topically. Suitable pharmaceutical carriers are known to those skilled in the art, such as saline or phosphate buffered saline. Topically, the anticoagulant or inhibitor can be administered in powdered or lyophilized form.

The dosage to be administered is that amount required to block greater than 90% of the potential activated protein C activity in human plasma, equivalent to the administration of 1 mg HPC4 (anti-protein C antibody)/kg body weight in patients. As demonstrated in the following example, this is the amount sufficient to saturate all the circulating protein C molecules at the time of treatment.

Although no pathological thrombosis was noted in the study described below, both grossly and histologically, in any of the animals, the possibility of pathologic thrombosis must certainly be considered whenever a systemic thrombogenic drug is utilized. Congenital deficiency of protein C is associated with several clinical diseases including venous thrombosis, warfarin-induced skin necrosis, pulmonary embolism, purpura fulminans neonatalis, and neonatal visceral venous thrombosis (Flaherty, M. J., et al. Iatrogenic immunization with bovine thrombin: A mechanism for prolonged thrombin times after surgery. *Ann. Int. Med.* 111: 631 (1989); Clouse, L. H. and Comp, P. C. The regulation of hemostasis: The protein C system. *N. Engl. J. Med.* 314(20): 1298 (1986); Preissner, K. T. Biological relevance of the protein C system and laboratories diagnosis of protein C and protein S deficiencies. *Clin. Sci.* 78: 351 (1990); Comp, P. C. Hereditary disorders predisposing to thrombosis. In B. S. Coller (Ed.), *Progress in Hemostasis and Thrombosis*. (New York: Grune and Stratton, 1986). Vol. 8, pp. 71-102; Tripodi, A., et al., Asymptomatic homozygous protein C deficiency. *Acta. Haematol.* 83: 152 (1990); Miletich, J., et al. Absence of thrombosis in subjects with heterozygous protein C deficiency. *N. Engl. J. Med.* 317(16): 991 (1987); Tuddenham, E. G., et al. Homozygous protein C deficiency with delayed onset of symptoms at 7 to 10 months. *Thromb. Res.* 53: 475 (1989)). The pattern of inheritance of protein C deficiency is autosomal dominant, yet in heterozygous individuals with protein C levels 30 to 80% of normal, thrombotic complications are often absent until adulthood when the physiological stress of illness, surgery, or pregnancy can potentiate a thrombotic episode. Homozygous-deficient individuals, however, often present in the neonatal period. Despite this strong clinical correlation between protein C deficiency and pathologic thrombosis, other authors report patients with both heterozygous and homozygous deficiencies of protein C with no clinical evidence of thrombosis. This suggests a multifactorial etiology of thrombosis in protein C-deficient patients not solely dependent on protein C levels. Doses of $HPC_4$ in this study were sufficient to saturate all the circulating protein C molecules at the time of treatment, yet titration of the dosage is possible so that inactivation of a specific fraction of the circulating protein C pool is achieved. To date, it is not known whether such a titration results in a scalable procoagulant effect; however, in inherited heterozygous-deficient individuals, the risk of thrombosis does roughly correlate to the severity of protein C deficiency suggesting adjustment of the procoagulant effect is possible. In normal individuals, the half-life of circulating protein C has been reported to be 6 to 15 hr (Kisiel, W. Human plasma protein C: Isolation, characterization and mechanism of activation by alpha-thrombin. *J. Clin. Invest.* 64: 761 (1979), Tuddenham, E. G., et al., Homozygous protein C deficiency with delayed onset of symptoms at 7 to 10 months. *Thromb. Res.* 53: 475 (1989)) allowing for adequate intrinsic replacement of antibody-bound protein C in 18 to 72 hr following a single dose of antibody. In the event of pathologic thrombosis following protein C blockade, normal protein C activity can be reestablished by administering extrinsic "pre"-activated protein C which is unaffected by any residual circulating monoclonal antibody (Preissner, K. T. Biological relevance of the protein C system and laboratories diagnosis of protein C and protein S deficiencies. *Clin. Sci.* 78: 351, 1990; Stearns, D. J., et al. The interaction of a $Ca^{2+}$-dependent monoclonal antibody with the protein C activation peptide region. Evidence for obligatory $Ca^{2+}$ binding to both antigen and antibody. *J. Biol. Chem.* 263: 826-832 (1988), Walker, F. J. Protein C deficiency in liver disease. *Ann. Clin. Lab. Sci.* 20(2): 106 (1990).

The dosage to be administered for the coagulant is between approximately 1000 to 10,000 units for thrombin and 0.1 to 10 mg for tissue thromboplastin. As used herein, tissue thromboplastin includes thromboplastin and purified tissue factor obtained by isolation from natural sources or by genetic engineering, alone or in combination with a source of phospholipid.

The present invention is further understood by reference to the following non-limiting example using an anti-protein C monoclonal antibody administered systemically or topically, alone or in combination with topical thrombin. The teachings of the specifically cited references are incorporated by reference herein.

Methods

Animal Model

Thirty-six domestic swine weighing 18±0.9 kg (means±SEM) were used in this study. Animals were initially tranquilized using an intramuscular (i.m.) injection of 7 mg/kg Telazol™ (A.H. Robins Co.) followed by placement of a 20-gauge intravenous catheter in an ear vein and a 5-ml sample of blood was removed fro hemoglobin determination. The animals were randomized in a blinded fashion into two groups receiving either activation ($HPC_4$) (obtained from Dr. Charles T. Esmon, Howard Hughes Medical Research Foundation and the Oklahoma Medical Research Foundation, ATCC No. 9892, Manassas, Va.) or an equal volume of intravenous saline. This dose of $HPC_4$ blocks protein C activation by greater that 95% when measured in a standard protein C activation assay (Taylor, F. B., et al., Protein C prevents the coagulopathic and lethal effects of *Escherichia coli* infusion in the baboon. *J. Clin. Invest.* 79: 918 (1987); Snow, T. R., et al. Protein C activation following coronary artery occlusion in the in situ porcine heart. *Circulation* 84: (1): 293 (1991), while the $HPC_4$ vehicle has been previously shown to have no significant procoagulant or anticoagulant effects.

The animals were then anesthetized with 10 mg/kg TELAZOL™ pain reliever and 4 mg/kg ROMPUN™ pain reliever (Mobay Corp.). The backs of each animal were then shaved and rectangles measuring 7×8 cm were drawn with a skin marker on each side of the midline with biopsy sites separated by a minimum of 3 cm. A Paget dermatome with a 7-cm-wide blade guard was then used to remove each skin graft measuring 0.015 inches in thickness. Immediately following skin removal, each site was sprayed with a 1.0 ml vol of saline, 1000 units thrombin (Parke-Davis), or tissue thromboplastin (Sigma Diagnostics). The surgeons were blinded to the identity of the topical treatments which were administered from covered, coded syringes, thus randomizing the wound sites on the backs of the animals. This design created six treatment groups: i.v. $HPC_4$-topical saline (n=34 sites), i.v. $HPC_4$-topical thrombin (n=11 sites), i.v. $HPC_4$-topical thromboplastin (n=12 sites), i.v. saline-topical saline (n=36 sites), i.v. saline-topical thrombin (n=12 sites), and i.v. saline-topical thromboplastin (n=12 sites). In each treatment group, after the topical treatment was applied, the sites were covered with saline moistened gauze sponges. The sponges were then removed 10 min later and the hemoglobin content of the sponge was measured.

Preparation of $HPC_4$ $HPC_4$ (Rabbit anti-mouse IgG monoclonal antibody to human protein C) was prepared as previously described (Stearns, D. J., et al. The interaction of a $Ca^{2+}$-dependent monoclonal antibody with the protein C activation peptide region. Evidence for obligatory $Ca^{2+}$ binding to both antigen and antibody. *J. Biol. Chem.* 263: 826-832 (1988); Esmon, C. T., et al. Interaction of thrombin with thrombomodulin. *Ann. N.Y. Acad. Sci.* 485: 215 (1986).

Hemoglobin Assay Measurement

Hemoglobin concentrations of whole blood were determined in each animal using an Instrumentation Laboratories 482 Co-oximeter from blood samples obtained from an ear vein at the beginning of the study. Blood loss from each surgical site was determined from the amount of hemoglobin contained in the gauze sponges removed from the wounds 10 min after placement. The sponges from each wound were placed in 500 ml of deionized water for a period of 30 min to allow hemolysis of the red blood cells. A sample of this fluid was then centrifuged at 10,000×g for 20 min followed by spectrophotometric assay at an optical density of 415 nm using a spectrophotometer (Micromedic Systems, Inc.). The hemoglobin content within each sponge was then calculated using the equation:

$$OD \times 0.1234 \times \text{deionized water volume(liters)} = \text{grams of } Hb \text{ per wound.}$$

The blood loss was calculated as:

$$\text{grams of } Hb \text{ per wound} \times Hb \text{ concentration(g/dl)} \times (100 \text{ ml/dl}) = \text{milliliter of blood loss.}$$

Pathological Evaluation

The wounds from six animals in the intravenous $HPC_4$ treatment group and six animals in the intravenous saline control group were covered with a transparent perforated adhesive dressing (UNIFLEX) reinforced by circumferential KERLIX gauze and VETWRAP adhesive dressing. The gauze and adhesive dressings were routinely changed every other day or more frequently if dislodged. Postoperative pain management was achieved using 0.005 mg/kg BUPRENEX™ pain reliever (Norwich-Easton). On the seventh postoperative day, the animals were given a 5000 unit bolus of heparin sodium (Upjohn Co.) to inhibit postmortem clotting, then euthanized 5 min later using pentobarbital. Skin graft sites were grossly examined for degree of healing and evidence of infection in each animal. Also, the superior and inferior vena cava, heart, and pulmonary vessels were examined grossly for evidence of preexisting thrombus formation. The lungs were then removed intact and insufflated with 10% buffered formalin and fixed for a period of 24 hr. Following fixation, 1-cm sections were made examining the lungs grossly for pulmonary emboli and/or infarction. Sections of this lung tissue were also obtained for histologic evaluation.

Statistical Analysis

The date comparing topical treatments within each intravenous treatment group were analyzed using the analysis of variance. A two-tailed Student t test was used to evaluate the two intravenous treatments when combined with saline topical controls. Differences were considered statistically significant when the probability level for a chance result was equal or less than 0.05.

Blood Loss Analysis

Figure 2:
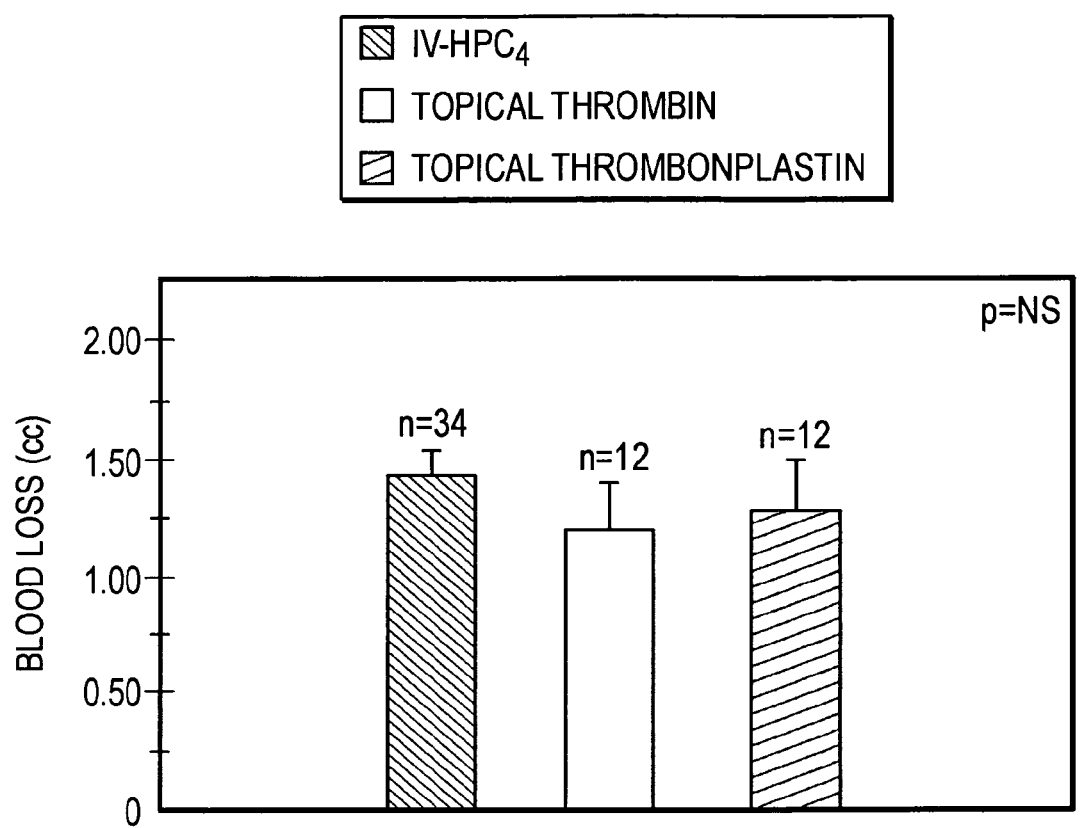
FIG. 2 is a graph of blood loss (cc) in i.v. HPC4, topical thrombin, and topical thromboplastin treated animals, comparing hemostasis with systemic $HPC_4$ blockade to topical treatments. Blood loss from each 7×8 cm surgical site is collected over 10 min and represented as mean milliliters±SEM. The solid black bar depicts animals receiving intravenous $HPC_4$ and topical saline (n=34 sites). The white bar represents animals receiving i.v. saline pretreatment then 1000 units topical thrombin to each surgical site (n=12 sites). The crosshatched bar represents animals receiving i.v. saline pretreatment then 1 ml of topical tissue thromboplastin (n=12 sites). Statistical analysis: ANOVA.

FIG. 1 demonstrates the hemostatic effect (mean blood loss±SEM) of intravenous $HPC_4$ compared to intravenous saline where all skin graft sites were treated topically with saline. $HPC_4$ significantly reduced blood loss from surgical sites an average of 27% compared to controls. When intravenous $HPC_4$ pretreatment is compared to the topical effects of thrombin or tissue thromboplastin alone, as shown in FIG. 2, each intervention affords a similar hemostatic effect.

Figure 3:
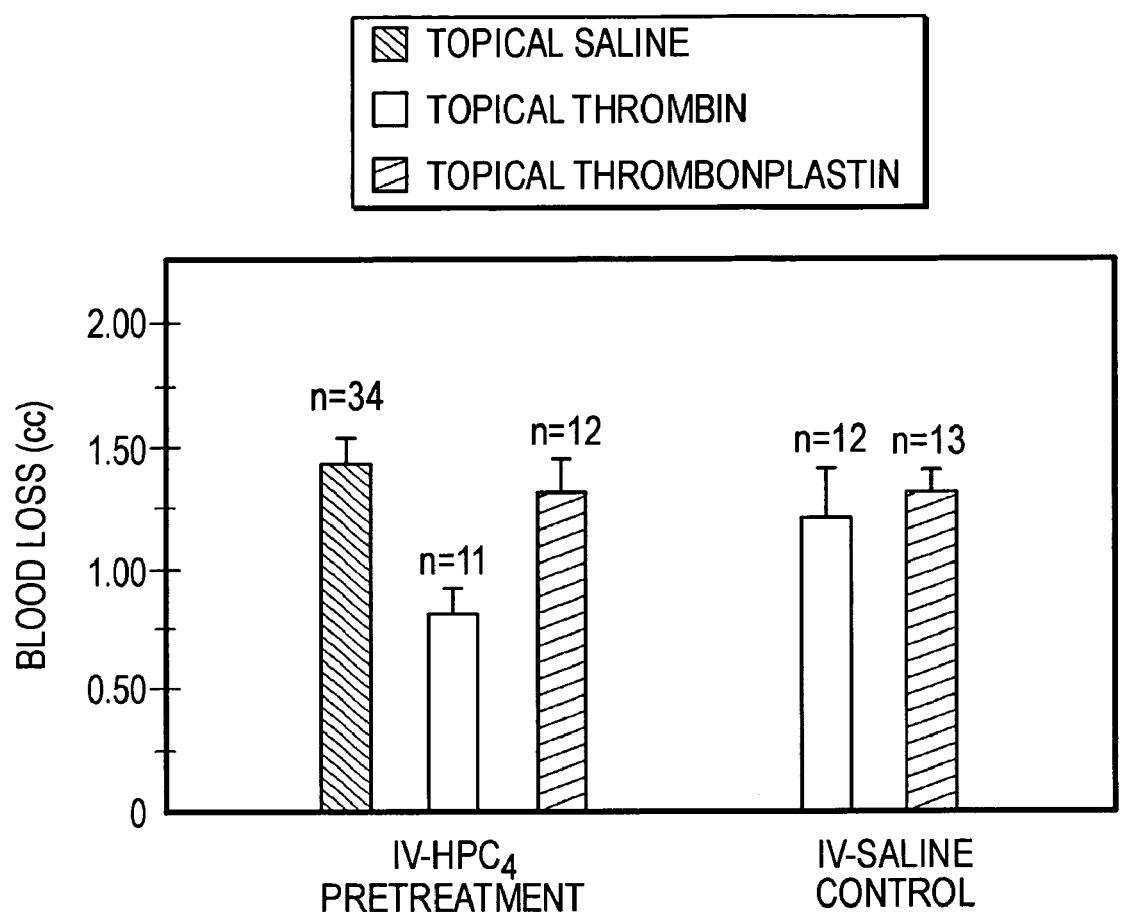
FIG. 3 is a graph of blood loss (cc) in i.v. HPC4 pretreatment and i.v. saline control treated animals, showing the synergistic effect of intravenous $HPC_4$ and topical thrombin. Blood loss from each 7×8 cm surgical site is collected over 10 min and represented as mean milliliters±SEM. The first three groups (left to right) received i.v. $HPC_4$ pretreatment followed by topical saline (n=34), thrombin (n=11), or tissue thromboplastin (n=12) applied to the surgical sites. The animals represented by the fourth and fifth bars (left to right) received i.v. saline pretreatment followed by either topical thrombin (n=12) or tissue thromboplastin (n=12). Statistical analysis: ANOVA.

Synergism between the $HPC_4$ antibody and the topical agents was also tested. Surgical sites treated with topical thrombin following pretreatment with $HPC_4$ had the lowest blood loss of any group within the study, as shown by FIG. 3. This synergistic effect resulted in a 44% decrease (P=<0.05) in blood loss compared to intravenous $HPC_4$ alone (solid black bar) and a 33% decrease (P=<0.05) in blood loss compared to topical thrombin alone (white bar in i.v. saline control group). No such synergistic effect was noted with topical tissue thromboplastin.

Gross and Histologic Data

Autopsies were performed on six of the animals in each of the intravenous treatment groups. All of these animals received only topical saline during the graft harvesting to eliminate any potential systemic effect the topical thrombogenic agents might have. Although wound healing was not a primary focus of this study, gross observation of the wound sites 7 days after surgery revealed complete reepithelialization of the partial-thickness graft sites of all animals with no visible differences noted between groups. No standardized, graded wound assessment was performed prior to autopsy, and as a result, no conclusions about early trends in wound healing can be made. Gross evidence of wound infection (erythema, calor, or exudate) was absent from all wounds observed at the time of autopsy. All animals were examined grossly for thrombi of the vena cava, heart, and pulmonary vessels postmortem and no evidence of pathological clotting was observed in either group. Gross examination of lung sections after insufflation with formalin also did not reveal any pathological thrombosis, nor did histologic sections.

This study demonstrates that the transient blockade of protein C activation provides a new systemic alternative to topical hemostatic measures that is safe and equally as effective as topical thrombin or tissue thromboplastin at their standard commercially available concentrations. In addition, the effects of protein C blockade work synergistically with topical thrombin treatment to provide a degree of hemostasis not achieved by either agent alone.

The design of this study, utilizing a preoperative treatment protocol in a skin graft model, was chosen because this is the first in vivo investigation of protein C blockade using a monoclonal antibody. These results can be applied to the clinical setting of grafting extensively burned patients. The results of this study demonstrate that blockade of protein C activation is a viable alternative to local hemostatic measures in a skin graft donor model and may have other applications in areas such as blunt and penetrating trauma, neurosurgery, and orthopedic surgery. Although the short- and long-term effects of creating a pharmacologically induced transient hypercoagulable state needs further study prior to widespread clinical use, these preliminary data suggest it to be free of short-term complications in a porcine model.

Modifications and variations of the method and compositions of the present invention will be obvious to those skilled in the art from the foregoing detailed description and are intended to come within the scope of the following claims.

---

---

We claim:

1. A method for inhibiting microvascular bleeding at a site in a patient exhibiting microvascular bleeding comprising administering to the patient an antibody to protein C in a pharmaceutically acceptable carrier in an effective amount to prevent anticoagulation by greater than 90% of activated protein C in human plasma.

2. The method of claim 1 further comprising the step of topically administering a coagulant at the site of bleeding.

3. The method of claim 2 wherein the topically administered coagulant is selected is selected from the group consisting of thrombin in a dosage of between approximately 1000 and 10,000 units and tissue factor in a dosage of between approximately 0.1 and 10 mg.

4. A method for inhibiting microvascular bleeding at a site in a patient exhibiting microvascular bleeding comprising systemically administering to the patient a monoclonal antibody to protein C which blocks protein C activation in a pharmaceutically acceptable carrier in an effective amount to prevent anticoagulation by great than 90% of activated protein C in human plasma.

5. The method of claim 4 wherein the antibody is HPC-4, deposited with the American Type Culture Collection, Manassas, Va. and assigned ATCC No. 9892.

* * * * *

UNITED STATES PATENT AND TRADEMARK OFFICE
CERTIFICATE OF CORRECTION

PATENT NO. : 7,291,333 B1
APPLICATION NO. : 08/323060
DATED : November 6, 2007
INVENTOR(S) : Philip C. Comp It is certified that error appears in the above-identified patent and that said Letters Patent is hereby corrected as shown below:

In claim 3, column 12, line 52, please delete "is selected is selected" and insert --is selected-- therefor.

In claim 4, column 12, line 61, please delete "great" and insert --greater-- therefor.

Signed and Sealed this

Twenty-ninth Day of April, 2008

JON W. DUDAS
*Director of the United States Patent and Trademark Office*